US009308063B2

United States Patent
Ferrilli

(10) Patent No.: US 9,308,063 B2
(45) Date of Patent: Apr. 12, 2016

(54) INCISOR TOOTH OR CANINE TOOTH, AND SET OF TEETH, AND METHOD FOR PRODUCING AND INCISOR TOOTH OR CANINE TOOTH

(75) Inventor: Antonio Ferrilli, Wängi (CH)

(73) Assignee: Ivoclar Vivadent AG, Schaan (LI)

( * ) Notice: Subject to any disclaimer, the term of this patent is extended or adjusted under 35 U.S.C. 154(b) by 795 days.

(21) Appl. No.: 12/288,519

(22) Filed: Oct. 21, 2008

(65) Prior Publication Data

US 2009/0104584 A1    Apr. 23, 2009

(30) Foreign Application Priority Data

Oct. 22, 2007  (DE) .......................... 10 2007 050 439

(51) Int. Cl.
A61C 13/09 (2006.01)
A61C 13/08 (2006.01)
A61C 13/097 (2006.01)

(52) U.S. Cl.
CPC ............... *A61C 13/09* (2013.01); *A61C 13/081* (2013.01); *A61C 13/097* (2013.01)

(58) Field of Classification Search
CPC ..... A61C 13/09; A61C 13/097; A61C 13/081
USPC ........... 433/167, 171, 197–198, 202.1–203.1, 433/218, 204, 219–223
See application file for complete search history.

(56) References Cited

U.S. PATENT DOCUMENTS

| | | | | |
|---|---|---|---|---|
| 2,300,305 A * | 10/1942 | Myerson | ................. | 433/211 |
| 3,218,711 A * | 11/1965 | Connan | ................. | 433/203.1 |
| 3,395,454 A * | 8/1968 | Frush | ................. | 433/203.1 |
| 3,449,832 A | 6/1969 | Connan | | |
| 5,308,243 A * | 5/1994 | Emmons | ................. | 433/203.1 |
| 5,624,262 A * | 4/1997 | Yarovesky et al. | ........... | 433/223 |
| 5,718,585 A | 2/1998 | Dehoff et al. | | |
| 5,800,164 A * | 9/1998 | Pfau | ................. | 433/26 |
| 5,989,031 A * | 11/1999 | Kura et al. | ................. | 433/202.1 |
| 6,488,503 B1 | 12/2002 | Lichkus | | |
| 6,755,646 B2 * | 6/2004 | Zun | ................. | 433/26 |
| 6,923,649 B2 | 8/2005 | Oswald et al. | | |
| 6,951,459 B2 * | 10/2005 | Weinstein | ................. | 433/26 |
| 7,086,863 B2 * | 8/2006 | Van der Zel | ................. | 433/223 |
| 2002/0175430 A1 | 11/2002 | Glidewell | | |
| 2008/0220395 A1* | 9/2008 | Marshall et al. | ............. | 433/215 |

FOREIGN PATENT DOCUMENTS

| | | |
|---|---|---|
| AT | 248607 | 8/1966 |
| DE | 3827657 A1 | 2/1990 |
| DE | 101 27 728 A1 | 12/2002 |
| DE | 10127728 A1 | 12/2002 |
| DE | 696 25 012 T2 | 10/2003 |
| EP | 1 121 908 A1 | 8/2001 |
| FR | 2 883 466 A1 | 9/2006 |
| GB | 1013548 | 12/1965 |

* cited by examiner

*Primary Examiner* — Cris L Rodriguez
*Assistant Examiner* — Hao D Mai
(74) *Attorney, Agent, or Firm* — Ann M. Knab; Thad McMurray

(57) ABSTRACT

The invention relates to an anterior tooth such as an incisor tooth or canine tooth built up in layers, with a cutting-edge material (30) at least partially covering a dentine material (28). At its occlusal end (38), the dentine material has projections (42) and/or irregularities (42, 46 and 48), which extend in the occlusal direction and correspond to 0.05 to 0.4 times the total length of a tooth.

21 Claims, 2 Drawing Sheets

INCISOR TOOTH OR CANINE TOOTH, AND SET OF TEETH, AND METHOD FOR PRODUCING AND INCISOR TOOTH OR CANINE TOOTH

CROSS-REFERENCE TO RELATED APPLICATIONS

This application claims foreign priority benefits under 35 U.S.C. §119(a)-(d) from German patent application ser. no. P 10 2007 050 439.1 filed Oct. 22, 2007.

TECHNICAL FIELD

The invention relates to anterior teeth such as an incisor tooth or canine tooth which is built up in layers, and more particularly to such a tooth wherein a cutting-edge material at least partially covers a dentine material, and to a method of making such a tooth.

BACKGROUND OF THE INVENTION

It has long been known for artificial teeth, in particular incisor teeth or canine teeth, to be built up from layers. In doing so, a cutting-edge material is built up such that it covers most of a dentine material, apart from the basal area of the dentine material. The dentine material can be joined to the cutting-edge material in any suitable way desired.

Thus, it is known from DE-A1 38 27 657, for example, to first build up a basic body of dentine material and then to injection-mold around the latter.

It is known, not only in plastic teeth, but also in ceramic teeth, to vary the layer thickness of the cutting-edge material in order to give an appearance resembling natural teeth. An example of this is the solution according to German specification 1 903 935.

The cutting-edge material is typically translucent, and the dentine material is somewhat opaque. It has also already been proposed, however, to increase the translucency of the dentine material. In this case, especially if a metal skeleton is used, a special opaquer is employed to veneer the metal skeleton. To provide the translucency, the cutting-edge material is often made quite thick. Although this gives the tooth the desired impression of translucency, it also gives the tooth a slightly "washed-out" look.

An improvement to these known solutions is known from DE 101 27 728. In the solution according to DE 101 27 728, the cutting-edge material is comparatively thin and has an uneven layer thickness. The uneven layer thickness is intended to improve the similarity to the natural tooth. However, this means that the tooth has a rather uneven effect specifically in the incisal area. The layer thickness should also not be chosen too small, in order to ensure that sprues that are used to produce the dentine material cannot be seen through the cutting-edge material. Such sprues are not very satisfactory from the technical point of view and also unsatisfactory from the esthetic point of view.

To improve the "technical" look of artificial teeth, attempts have therefore been made, in the recent years and decades, to improve the similarity to the natural appearance by using specific colorations. Mention may be made here of the known painting technique, which is still used regularly even today, even though it is very much dependent on the skill of the dental technician and is labor-intensive.

Moreover, it has also already been proposed to incorporate a color gradient within the layers. This solution, however, is extremely difficult to implement on account of the technical difficulties involved, especially since it is necessary to establish an exact reference point, which is a spatial one and is therefore difficult to define.

To remove plastic bodies from molds, it has become known to select the mold separation lines such that the fewest possible undercuts are present. Typically, the removal of mold halves with undercuts typically requires the provision of complicated slides, which also impair the precision. Also in light of these considerations, typical teeth, particularly plastic teeth, are generally produced free of undercuts and tapering obliquely toward the incisal side, the mold separation taking place at the "thickest" point of the tooth which, in the case of incisor teeth, may be arranged relatively near to the incisal area. This too has led to rather smooth and straight surfaces.

OBJECTS AND SUMMARY OF THE INVENTION

Against the background of these disadvantages, the object of the invention is to create an anterior tooth which is built up in layers, the dentine material at its occlusal end having projections and/or irregularities which extend in the occlusal direction, and which, while being easy to produce and aesthetically much improved, still gives an appearance approximating the natural teeth.

According to the invention, it is particularly expedient that the incisor tooth or canine tooth built up in layers according to the invention is not subject to fixed specifications in terms of its outer shape. Thus, it is possible, in an incisor tooth, to provide a substantially straight or at most slightly undulated incisal cutting edge of the cutting-edge material. This represents a considerable advance compared to a markedly undulated design, as has already been sought to achieve a natural appearance.

Thus, according to the invention, the undulation or irregularity of the outer cutting edge can be less than 30%, in particular less than 20% and preferably approximately 10% of the layer thickness of the cutting-edge material at this point.

However, this does not prevent the design according to the invention with projections and/or irregularities extending in the occlusal direction. According to the invention, the projections and/or irregularities of the dentine material, that is to say of the boundary layer between the dentine material and cutting-edge material, over a certain predetermined height, which is different than 0 and much less than half of the total length of a tooth. The height of the irregularities or projections can, for example, be only $1/20$ of the height of the tooth. This is expedient, for example, if a very small layer thickness is realized for the cutting-edge material, which can again amount for example to $1/10$ or even also $1/20$ of the height of a tooth. However, the height of the irregularities can also be chosen substantially greater, which is expedient if the layer thickness of the cutting-edge material is chosen substantially greater, for example 20% or even 30% of the tooth height, in order to improve the translucency.

According to the invention, the thickness of the cutting-edge material and the height of the projections and/or irregularities are to this extent correlated with one another, it being particularly expedient if the thickness of the cutting-edge material, with a small projection height, is slightly greater, and, with a large projection height, slightly smaller than the projection height.

According to the invention, it is surprisingly possible, by simple means, to hugely improve the optical properties of the incisor teeth or canine teeth, specifically such that a washed-out impression and also too "technical" an impression are avoided.

According to the invention, it is particularly expedient that the invention makes it possible to work with a comparatively large layer thickness for the cutting-edge materials, with an aesthetically very pleasing effect. The layer thickness can, for example, expediently be at least 20% of the length of a tooth. This permits a mechanically improved design, since too thin layer thicknesses are technically more difficult to handle, especially if the adherence between cutting-edge material and dentine material cannot easily be overcome, because of the different chemical substances from which they are built up, for example if different ceramic types (zirconium oxide or silicate ceramics) are used. It has also been found that the greater layer thickness improves the stability with respect to different coefficients of thermal expansion, which are in most cases very problematic in different ceramics.

The tendency of the cutting-edge material to chip off is surprisingly much lower, and, according to the invention, the realization of irregularities also having a supporting effect here, since in this way the adherence also appears to be improved.

The realization of irregularities at the boundary layer between cutting-edge material and dentine material has a dual function. The fact that an advance can be achieved to this extent is surprising since the roughness of ceramic surfaces is known per se, and it is particularly expedient according to the invention if neither the cutting-edge material at its interface to the dentine material nor the dentine material at its interface to the cutting-edge material is subjected to machining operations. Rather, it is preferable in this connection to use a specially designed core mold for shaping the boundary layer, the core mold having, at its incisal or occlusal end, the surface structure and projections and irregularities that the interface between dentine material and cutting-edge material is later intended to have.

This production is preferred if first the cutting-edge material and then the dentine material is cast for realizing the tooth according to the invention.

Alternatively, layering from the inside outward is also possible. In this method, a core mold is first cast for the dentine material, its inner profile again corresponding exactly to the interface between cutting-edge material and dentine material. Thereafter, the cast dentine material itself is used as inner mold for the cutting-edge material, and the cutting-edge material is introduced into the resulting layered mold cavity, the irregularities once again achieving a particularly good anchoring especially also in the strongly loaded incisal area of the tooth.

The solution according to the invention is particularly well suited for realization of ceramic teeth. While plastic material, because of the used material, is easier to produce, since plastic is relatively elastic compared to ceramic and therefore better tolerates inner stresses, it is possible according to the invention, by surprisingly simple means, to solve the problem of realizing a ceramic with natural appearance without generating technical problems.

According to the invention, it is also particularly expedient to combine a relatively hard dentine material with a by contrast softer cutting-edge material. Different materials can also be realized because of the good anchoring, and the use of a softer cutting-edge material has the advantage that the antagonist of the restored tooth is less strongly affected.

BRIEF DESCRIPTION OF THE FIGURES

Further advantages, details and features will become clear from the following description of two illustrative embodiments, with reference being made to the drawings, in which.

DETAILED DESCRIPTION

Figure 1:
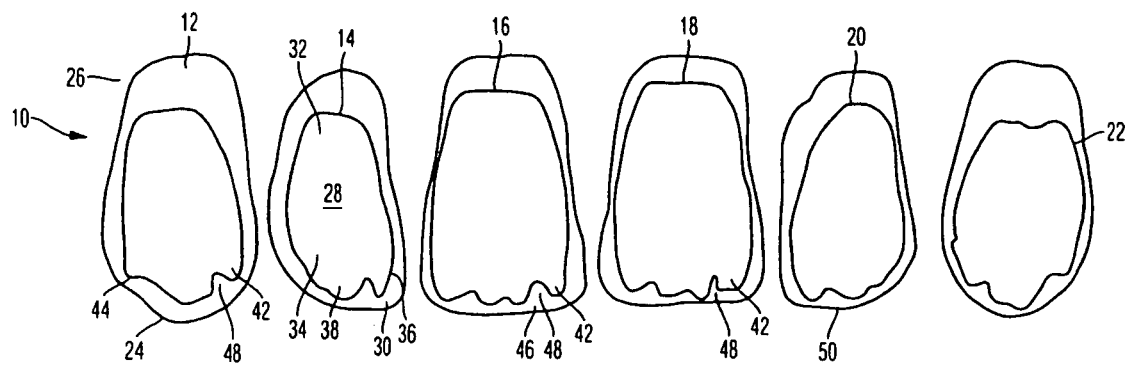
FIG. 1 shows an illustrative embodiment of a set of anterior teeth including incisor teeth and canine teeth configured according to the invention.

FIG. 1 shows, by way of example, one embodiment of a set of teeth according to the invention for the upper jaw, with four incisor teeth and two canine teeth. The set 10 of teeth comprises a canine tooth 12, four incisor teeth 14, 16, 18 and 20, and a further canine tooth 22. The view shows in each case a section through the tooth in the area of its greatest extent. Each tooth has an incisal cutting edge 24 and extends between this cutting edge and the basal end 26 in a manner known per se from the basic form.

For simplicity, the incisor tooth 14, which is to be regarded as tooth II, will be considered here. The tooth 14 is basically built up of dentine material 28 which, in the illustrative embodiment shown, is completely surrounded by cutting-edge material 30. Although the cutting-edge material in the illustrative embodiments shown here extends also over the basal end 26, it will be appreciated that it is also possible to provide the dentine material there.

In the illustrative embodiment shown, the cutting-edge material accordingly extends in the manner of a three-dimensional cover layer around the dentine material 28. The dentine material 28 extends over its buccal end area 32 and its distal and mesial side faces 34 and 36, respectively, in each case substantially straight, apart from a slight bulge or, if appropriate, a slight undulation.

By contrast, according to the invention, the occlusal or incisal end area 38 of the dentine material is strongly undulated. The undulation or the provision of irregularities there corresponds to a height which, in the example shown, corresponds at most to 6% of the height of the tooth.

The dentine material 28 is also completely covered by the cutting-edge material 30 there. The layer thickness there, that is to say in the occlusal area, corresponds on average to once again approximately 6% of the height of the cutting-edge material. It is preferable that the undulation or the formation of irregularities is quite intensive, but in each case provided with radii. Thus, the maximum inclination angle 40 of oblique surfaces in the area of the occlusal interface between cutting-edge material and dentine material is approximately 60% in the incisor tooth 14. Mainly, however, the inclination angle 40 is much smaller, and typically lies at 10% to 20%.

The minimum layer thickness of the cutting-edge material 30 in the incisal end area 38 is 4% of the tooth height.

The values specified above can be varied between individual incisor or canine teeth and also between individual sets of teeth, in order to obtain an impression that is life-like and very similar to the natural appearance of the teeth.

Thus, the minimum layer thickness in the incisal area of the cutting-edge material 30 is 8% for the canine tooth 12. At one location there, a distinct projection 42 is provided, whereas otherwise there is only a slightly undulated configuration of the boundary layer 44 between cutting-edge material and dentine material in the incisal area.

By contrast, the minimum layer thickness of the cutting-edge material 30 in the incisal area 46 of the tooth 18 is only 1% of the tooth height; a quite intensively formed fissure 48 is provided, which laterally divides off a projection 42 in the mesial or distal direction.

Similar configurations are provided for the teeth 16, 20 and 22, the views shown in the figures pointing to examples of possible deviations.

Figure 2:
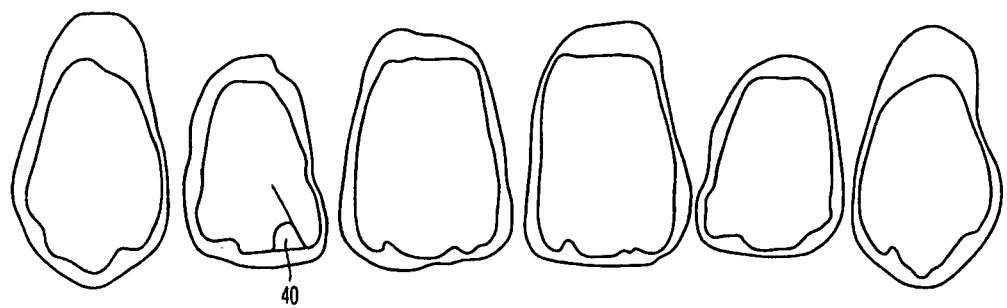
FIG. 2 shows another embodiment of a further set of incisor teeth and canine teeth configured according to the invention.

FIG. 2 shows a similar set of teeth. In this set of teeth, the undulation and intensity of the projections is generally less pronounced, such that irregularities extend less in terms of depth or height. Here, the minimum layer thickness is 1 mm.

In a manner known per se, the opacity of the dentine material 28 is greater than the opacity of the cutting-edge material 30. The irregularities 42, 46 and 48 alternate, and smaller and greater radii are likewise provided. The irregularities are asymmetrical fissures, incisions, or trenches formed in the dentine material (28) and filled by cutting-edge material (30). Moreover, the irregularities do not extend only in the direction of the drawing, but also in the direction perpendicular to the drawing. It is also possible for the strong irregularities in the boundary layer 44 to be followed by an irregularity reduced to ⅓ or even to 1/10 in the area of the incisal cutting edge. In this way, it is still possible to obtain a substantially straight cutting edge, which nevertheless resembles a natural tooth shape.

Figure 3:
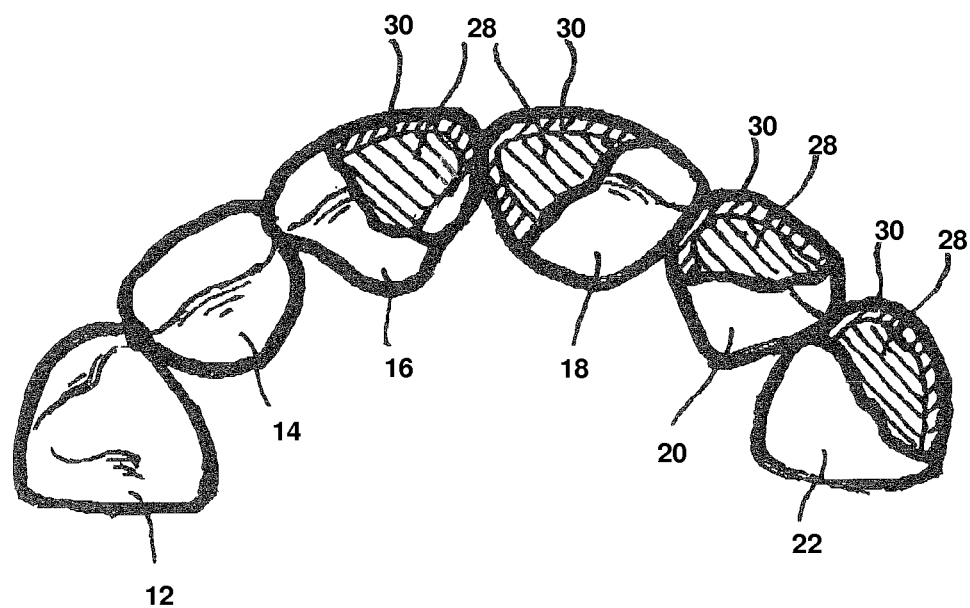
FIG. 3 is a top view of incisor teeth according to this invention.

FIG. 3 shows first and second incisor teeth 14, 16, 18, 20 and canine teeth 12, 22 in top view. The dentine material 28 for forming the first and second incisor teeth 14, 16, 18, 20 has radial, in particular mesial, and with respect to the first incisor teeth 16, 18 also distal, bulge which follows a corresponding bulge of the cutting-edge material 30 on the outer shape of the cutting-edge material 30 at this location. Adjacent to this bulge, the dentine material 28 is set back toward the interior of the tooth, seen in the front view of the tooth.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. Sets of artificial teeth comprising a plurality of individual detached teeth, where each individual tooth of the plurality of individual detached teeth is built up in two layers consisting of a cutting edge material and a dentine material, with the cutting-edge material at least partially covering the dentine material, wherein the dentine material (28) comprises an occlusal end (38) having irregularities (42, 46 and 48), wherein a length of each of the irregularities extends in an occlusal direction and corresponds to 0.05 to 0.4 times a total length of the tooth, wherein the irregularities create an incisal dentine profile, and wherein the dentine material (28) has the irregularities (42, 46 and 48), at least in the occlusal end (38) of the dentine material (28), wherein a surface of the dentine material forms a boundary layer between the dentine material and the cutting-edge material, wherein the irregularities comprise fissures, incisions or trenches that are asymmetrical, wherein the incisal dentine profile is different in each tooth of the set of teeth, and wherein the irregularities have oblique surfaces having thicknesses and angles of inclination wherein values of the thicknesses of the irregularities and angles of inclination of the irregularities vary between individual teeth and between sets of teeth.

2. Sets of artificial teeth as claimed in claim 1, wherein a length of each of the irregularities (42, 46 and 48) extend in the occlusal direction over at least ⅓, of the total length of the tooth.

3. Sets of artificial teeth as claimed in claim 1, wherein the irregularities (42, 46 and 48) are designed in a form of depressions and/or elevations, which extend substantially parallel to a longitudinal extent of the tooth.

4. Sets of artificial teeth as claimed in claim 3, wherein the depressions are of different depths and/or the elevations are of different heights.

5. Sets of artificial teeth as claimed in claim 1, wherein the incisal dentine profile is different when compared to teeth of different tooth shapes.

6. Sets of artificial teeth as claimed in claim 1, wherein the irregularities (42, 46 and 48) are located in the boundary layer (44) between cutting-edge material (30) and dentine material (28).

7. Sets of artificial teeth as claimed in claim 1, wherein the dentine material (28) has a greater opacity than the cutting-edge material (30).

8. Sets of artificial teeth as claimed in claim 1, wherein the irregularities (42, 46 and 48) are distributed over an interface between dentine material (28) and cutting-edge material (30).

9. Sets of artificial teeth as claimed in claim 8, wherein irregularities (42, 46 and 48) in the boundary layer (44) between cutting-edge material (30) and dentine material (28) are designed with a curved structure having radii that change over the profile of the irregularities (42, 46 and 48).

10. Sets of artificial teeth as claimed in claim 8, wherein irregularities (42, 46 and 48) are designed in an undulating shape which extend over the surface of the substantially stump-shaped dentine material (28) and are filled by the cutting-edge material (30).

11. Sets of artificial teeth as claimed in claim 8, wherein an irregularity (42, 46 and 48) in the boundary layer (44) between dentine material (28) and cutting-edge material (30) is followed by an irregularity (42, 46 and 48) on the surface of the cutting-edge material (30).

12. Sets of artificial teeth as claimed in claim 8, wherein the fissures (48), incisions or trenches formed in the dentine material (28) are filled by cutting-edge material (30).

13. Sets of artificial teeth as claimed in claim 8, wherein the dentine material (28) for forming a first and second incisor teeth (14, 16, 18 and 20) has a radial, and with respect to the first incisor teeth (14, 16, 18 and 20) also distal, bulge, which follows a corresponding bulge of the cutting-edge material (30) on the outer shape of the cutting-edge material (30) at this location, and wherein, adjacent to this bulge, the dentine material (28) is set back toward the interior of the tooth, seen in the front view of the tooth.

14. Sets of artificial teeth as claimed in claim 8, wherein the cutting-edge material (30) in the area of irregularities (42, 46 and 48) has a thickness of less than 2 mm, and irregularities (42, 46 and 48) of the dentine material (28) can be seen through the cutting-edge material (30) because of translucency or transparency of the cutting-edge material.

15. Sets of artificial teeth as claimed in claim 8, wherein the dentine material (28) has a greater opacity and greater brilliancy than the cutting-edge material (30).

16. Sets of artificial teeth as claimed in claim 8, wherein dentine material (28) is backed by an opaquer, which finishes a skeleton on which the dentine material (28) is applied or is to be applied.

17. Sets of artificial teeth as claimed in claim 1, wherein the lengths of the irregularities (42, 46 and 48) extend in the occlusal direction over at least ¼ of the total length of the tooth.

18. Sets of artificial teeth as claimed in claim 8, wherein the irregularities (42, 46 and 48) are distributed over an interface between dentine material (28) and cutting-edge material (30), in several dimensions, and wherein the irregularities are designed with a curved structure with smaller and greater radii alternating in the irregularities (42, 46 and 48).

19. Sets of artificial teeth as claimed in claim 8, wherein irregularities (42, 46 and 48) in the boundary layer (44) between cutting-edge material (30) and dentine material (28) are designed with a curved structure having radii that change the profile of the irregularities (42, 46 and 48) and are smaller than ten times a tooth length and greater than a tenth of a tooth length.

20. Sets of artificial teeth as claimed in claim 8, wherein irregularities (42, 46 and 48) are designed in an undulating shape, as two-dimensional waves, which extend over the surface of the substantially stump-shaped dentine material (28) and are filled by the cutting-edge material (30).

21. Sets of artificial teeth as claimed in claim 8, wherein the dentine material (28) for forming the first and second incisor teeth (14, 16, 18 and 20) has a mesial, and with respect to the first incisor teeth (14, 16, 18 and 20) also distal, bulge, which follows a corresponding bulge of the cutting-edge material (30) on the outer shape of the cutting-edge material (30) at this location, and wherein, adjacent to this bulge, the dentine material (28) is set back toward the interior of the tooth, seen in the front view of the tooth.

\* \* \* \* \*